United States Patent [19]
Kodali et al.

[11] Patent Number: 6,051,539
[45] Date of Patent: Apr. 18, 2000

[54] PROCESS FOR MODIFYING UNSATURATED TRIACYLGLYCEROL OILS RESULTING PRODUCTS AND USES THEREOF

[75] Inventors: Dharma R. Kodali, Plymouth; Keqiang Li, St. Paul, both of Minn.

[73] Assignee: Cargill, Inc., Deephaven, Minn.

[21] Appl. No.: 09/108,773

[22] Filed: Jul. 2, 1998

[51] Int. Cl.$^7$ .................. C10M 105/38; C10M 107/20
[52] U.S. Cl. .................. 508/491; 508/485; 560/124; 554/24; 252/79
[58] Field of Search .................. 508/491, 485; 560/124; 554/24

[56] References Cited

U.S. PATENT DOCUMENTS

| | | | |
|---|---|---|---|
| 4,472,313 | 9/1984 | Giger | 260/410 |
| 4,500,541 | 2/1985 | Hausberg et al. | 514/466 |
| 5,229,023 | 7/1993 | Landis | 560/127 |
| 5,427,704 | 6/1995 | Lawate | 508/491 |
| 5,773,391 | 6/1998 | Lawate et al. | 508/257 |
| 5,936,139 | 8/1999 | Schmid | 800/281 |

FOREIGN PATENT DOCUMENTS

| | | |
|---|---|---|
| 0 712 834 A1 | 5/1996 | European Pat. Off. . |
| 58-147498 | 9/1983 | Japan . |
| 1005641 | 9/1965 | United Kingdom . |

OTHER PUBLICATIONS

Deyrup J. A. et al., "The Isomeric trans, trans–Bicyclo [6.1.0]non–4–enes," *J. Org. Chem.*, vol. 40, No. 3, pp. 284–289 (1975).

Gensler, W. J. et al., "Structure Determination of Cyclopropane—Substituted Acids by Mass Spectrometry," *J. Org. Chem.*, vol. 42, No. 1, pp. 126–129 (1977).

Jie, M.S. et al., "Preparation and properties of gem–dichlorocy cloporpane derivatives of long–chain fatty esters," *Lipids*, vol. 27, No. 1, (1992)—Abstract p. 827 only.

Blanchet, et al., "Chromatographie en Phase Gazeuse et Lipochimie", *Olégineux*, 21° année, No. 12:749–752 (Décembre 1966).

Christie, W. W. et al., "Mass Spectrometry of Lipids. I. Cyclopropane Fatty Acid Esters", *Lipids*, 1:176–182 (1966).

Christie, W. W. et al., "Fatty Acids, Part 17. The Synthesis and Chromatographic and Spectroscopic Properties of the Cyclopropane Esters Derived from All the methyl Octadecenoates", *Chem. Phys. Lipids* 2: 196–202 (1968).

Doering et al., "The Electron–seeking Demands of Dichlorocarbene in its Addition to Olefins", *Jour. of the Amer. Chem. Soc..*, 80:5274–5277 (1958).

Landgrebe, J. et al., "A Stabilized Cyclopropyl Cation. Synthesis and Solvolysis of 1–Chlorobicyclopropyl", *Journal of the American Chemical Society*, 90:2395–400 (Jan. 17, 1968).

LeGoff, Eugene, "Cyclopropanes from an Easily Prepared, Highly Active Zine–Copper Couple, Dibromomethane, and Olefins", *Notes*, 29:2048–2049 (1964).

le Noble, William J., "The Effect of Pressure on the Hydrolysis of Chloroform, Chlorodifluoromethane, and 3–Chloro–3–methylbutyne. The Nature of the Intermediates", *Jour. of the Amer. Chem. Soc.*, vol. 87 (1965).

March, Jerry, "Reactions, Mechanisms, and Structure", *Advanced Organic Chemistry*, 3$^{rd}$ Ed., 173–176:768–773 (1985).

Overbenger, C. G. et al., "Monomers and Polymers, a Synthesis of Vinyl Cyclopropane and Dicyclopropyl[1]", *Notes*, 28:867–868 (Mar., 1963).

(List continued on next page.)

*Primary Examiner*—Ellen M. McAvoy
*Attorney, Agent, or Firm*—Merchant & Gould P.C.

[57] ABSTRACT

A process for modifying an unsaturated polyol fatty acid ester stock, such as an unsaturated triacylglycerol oil, to enhance its fluidity and/or oxidative stability is provided. The method includes reacting the unsaturated polyol fatty acid ester stock with cyclopropanating agent. Lubricants containing a modified unsaturated polyol fatty acid ester and methods for their production and use are also provided.

39 Claims, 6 Drawing Sheets

DSC SPECTRUM OF TRIOLEOYL GLYCEROL

OTHER PUBLICATIONS

Shortridge, R. W. et al., "The Synthesis of Some Cyclopropane and Spirane Hydrocarbons[1]", *Synthesis of Some Cyclopropane and Spirane Hydrocarbons*, 70:946–949 (Mar. 1948).

Simmons, Howard E. et al., "Cyclopropanes from Unsaturated Compounds, Methylene Iodide, and Zinc–Copper Couple", *Organic Reactions*, 20:1–131 (1973).

Skell, Philip S. et al., "Reactions of Bivalent Carbon Compounds. Reactivities in Olefin–Dibromocarbene Reactions" *Journ. of the Amer. Chem. Soc.*, 78:5430–5433 (Oct. 20, 1956).

Wood, Randall et al., "Cyclopropane Fatty acid Metabolism: Physical and Chemical Identification of Propane Ring Metabolic Products in the Adipose Tissue", *Journ. of the Amer. Oil Chem. Soc.*, 42:315–320 (Apr. 1965).

Woodworth, Curtis W. et al., "Hydrogenolysis of Cyclopropane Derivatives. Application to the Synthesis of an Axial t–Butylcyclohexane, 2–t–Butyladamantane", *Chemical Communications*, pp. 569–570 (1968).

Bianchini, J. P. et al., "Determination of Cyclopropenoic and Cyclopropanoic Fatty Acids in Cottonseed and Kapok Seek Oils by Gas–Liquid Chromatography," *Analytical Chemistry*, 53(14):2194–2201 (Dec. 1981).

Christie, W. W. , "Cyclopropane and Cyclopropene Fatty Acids," *Topics in Lipid Chemistry*, vol. I, pp. 1–49 (1970).

Gaydou, E. M. et al., "Fatty Acid Composition of Sterculia Seeds and Oils from Madagascar," *J. Agric. Food Chem.* 41(1):64–66 (1993).

Kenney, H. E. et al., "Preparation and Etherification Reaction of Fatty Dichlorocyclopropanes," *The Journal of American Oil Chemists Society.* 41:82–85 (Jan. 1964).

Nachtman, E. S. et al., "Lubricants and Lubrication in Metalworking Operations,", Copyright © Marcel Dekker, Inc., cover pages and pp. 95, 96, 100 and 101 (1985).

Qin, Y. et al., "Effects of the Essential Oil from Litchi Seed on the Serum Lipids Metabolism of Hypercholesterol Rats," *Food Science*, 16(9):56–59 (1995).

Ralaimanarivo, A. et al., "Fatty Acid Composition of Seed Oils from Six*Adansonia Species* with Particular Reference to Cyclopropane and Cyclopropene Acids," *Lipids*, 17(1), contents page and pp. 1–10 (Jan. 1982).

Rao, K. S. et al., "Fatty Acid and Amino Acid Compositions of *Brachychiton discolor, Brachychiton diversifolius,* and *Brachychiton acerifolius* Seeds," *J. Agric. Food. Chem.*, 37(4):916–920 (1989).

Rao, K. S., "Characteristics and Fatty Acid Composition of Brachychiton Species Seeds and the Oils (Sterculiaceae),"*J. Agric. Food Chem.* 39(5):881–882 (1991).

Vickery. J.R., "The Occurrence of Dihydromalvalic Acid in Some Seed Oils," *JAOCS*, 58(6):731–732 (Jun. 1981).

Oil Stability Index (OSI), AOCS Official Method Cd 12b–92, pp. 1–5 revised 1993).

osi. The Oxidative Stability Instrument, Owners Manuel, 3 pgs. (Oct. 1992) revised Mar. 1993.

FIG. 3 TRIOLEOYL GLYCEROL BEFORE AND AFTER OSI MEASUREMENT

FIG. 4 CYLOPROPANATED TRIOLEOYL GLYCEROL BEFORE AND AFTER OSI MEASUREMENT

FIG. 5 IMC-130 WITH 1% TBHQ BEFORE AND AFTER OSI MEASUREMENT

FIG. 6 CYLOPROPANATED IMC-130 WITH 1% TBHQ BEFORE AND AFTER OSI MEASUREMENT

PROCESS FOR MODIFYING UNSATURATED TRIACYLGLYCEROL OILS RESULTING PRODUCTS AND USES THEREOF

BACKGROUND OF THE INVENTION

Vegetable oils are obtainable in large volumes from renewable resources and in general are characterized as readily biodegradable or "environmentally friendly". As a result, such oils and related unsaturated polyol fatty acid ester stocks are potentially attractive for use in a wide variety of applications.

With respect to use for lubrication purposes, especially as machine lubricants, vegetable oils have not been fully desirable. Many vegetable oils do not possess the desired spectrum of characteristics relating to: pour point; oxidative stability; and compatibility with additives among others. Vegetable oils do however possess many desirable properties for use as a lubricant. In particular, vegetable oils typically provide good boundary lubrication, good viscosity, high viscosity index and high flash point. In addition, vegetable oils are generally nontoxic and readily biodegradable. For example, under standard test conditions (e.g., OCED 301D test method), a typical vegetable oil can biodegrade up to 80% into carbon dioxide and water in 28 days, as compared to 25% or less for typical petroleum-based lubricating fluids.

Two characteristics, which are often major limitations to the utilization of vegetable oils as lubricants, relate to stability and low temperature behavior. In particular, vegetable oils often contain substantial amounts of unsaturation (i.e., one or more carbon—carbon double bonds distributed along the fatty acyl chains). The sites of unsaturation may be associated with sufficient oxidative reactivity to render the oils insufficiently stable for use as lubricants. If efforts are made to reduce the unsaturation, for example by hydrogenation, generally undesirable changes in pour point and/or viscosity index result.

SUMMARY OF THE INVENTION

The present invention relates to modified unsaturated polyol fatty acid ester stocks such as unsaturated triacylglycerol oils. It particularly concerns modifications of selected vegetable oils to produce liquid products with preferred properties for use, for example as lubricant base stocks or in related uses. The unsaturated triacylglycerol polyol fatty acid ester stocks are typically derived from plants, such as an oil seed, or animal sources, such as tallow.

A process for modifying an unsaturated polyol fatty acid ester stock, such as an unsaturated vegetable oil stock, to enhance its fluidity and/or oxidative stability is provided. The process includes reacting the unsaturated polyol fatty acid ester stock with cyclopropanating agent to form a cyclopropanated product. The cyclopropanated product formed from the reaction with the cyclopropanating agent includes polyol fatty acid ester (e.g., triacylglycerols) which have at least one fatty acyl chain modified to include a cyclopropyl group. It will be understood that the cyclopropanation of the starting ester stock will not necessarily be uniform, but rather may result in cyclopropanation of some fatty acyl chains and not of others. If desired, the cyclopropanated product may be fractionated using conventional techniques to alter the spectrum of modified and unmodified esters present. For example, the cyclopropanated product may be fractionated to remove at least a portion of the saturated esters, thereby enhancing the fluidity properties of the fractionated cyclopropanated product with respect to the cyclopropanated product.

The term "unsaturated polyol fatty acid ester stock" as used herein refers to fatty acid esters of alcohols which include two or more hydroxy groups ("polyols"). At least some and, typically, a majority (i.e., more than 50%) of the fatty acyl chains include at least one unsaturated carbon—carbon bond. The mixture of fatty acids isolated from complete hydrolysis of a specific unsaturated polyol fatty acid ester stock is referred to herein as a "fatty acid composition." In other words, by the term "fatty acid composition" reference is made to the identifiable fatty acids derived from the fatty acyl residues in the various polyol esters in a given stock. The present unsaturated polyol fatty acid ester stocks typically include esters of a mixture of fatty acids, e.g., a mixture of saturated and unsaturated fatty acids.

Herein, when reference is made to the terms "unsaturated triacylglycerol oil" or "unsaturated triacylglycerol stock," the intent is to refer to a material comprising triacylglycerols, whether altered or not, derived from various plant and animal sources, such as oil seed sources. The unsaturated triacylglycerol oil may also be produced synthetically, e.g., via a reaction between glycerol with fatty acid and/or fatty acid alkyl esters at least a portion of which include unsaturated fatty acyl chains. The term at least includes within its scope: (a) such materials which have not been altered after isolation; (b) materials which have been refined, bleached and/or deodorized after isolation; (c) materials obtained by a process which includes fractionation of an unsaturated triacylglycerol oil; and, also, (d) oils obtained from plant or animal sources and altered in some manner, for example through partial hydrogenation. It will be understood that the unsaturated triacylglycerol oil may include a mixture of triacylglycerols, and a mixture of triacylglycerol isomers. By the term "triacylglycerol isomers", reference is meant to triacylglycerols which, although including the same esterified acid residues, may vary with respect to the location of the residues in the triacylglycerol. For example, an unsaturated triacylglycerol oil such as a vegetable oil stock can include both symmetrical and unsymmetrical isomers of a triacylglycerol which includes two or three different fatty acyl chains (e.g., includes both stearate and oleate groups). This can include triacylglycerol isomers that contain trans as well cis unsaturation and combinations thereof.

Herein, the result of adding cyclopropanating agent to an unsaturated polyol fatty acid ester stock, such as vegetable oil stock, will be referenced as an "cyclopropanated product." The term "cyclopropanated product" includes within its scope practices which involve adding one or more cyclopropanating agents (e.g., reagent(s) capable of adding methylene to a carbon—carbon double bond to form a cyclopropyl group), on an average per molecule basis, to the unsaturated polyol fatty acid ester stock. As used herein, the term "cyclopropyl group" refers to an adduct produced by the reaction of cyclopropanating agent with a carbon—carbon double bond, such as a double bond in a fatty acyl chain of a triacylglycerol, to add a methylene moiety and form a three membered ring. One example of a cyclopropanated product is the adduct produced by a Simmons-Smith reaction between $CH_2Br_2$ or $CH_2I_2$ and double bonds in the fatty acyl chain of a vegetable oil. Of course, it will be understood that the cyclopropanation of the unsaturated polyol fatty acid ester stock will not necessarily be uniform in the mixture, but rather the result of the addition may be cyclopropanation of some fatty acyl chains and not to others. Nor will the cyclopropanated product necessarily include the formation of at least one (on an average molecular basis) cyclopropyl group per ester molecule. For example, the cyclopropanated product of a vegetable oil stock may often include a number of unmodified triacylglycerols, i.e., triacylglycerols with fatty acyl chains lacking a cyclopropyl group.

The cyclopropanated polyol fatty acid ester stocks have an oxidative stability (as evidenced by their "Oxidized Viscosity Index" ("OVI"; as defined herein) and/or active methylene content) which is enhanced with respect to the oxidative stability of the corresponding unmodified unsaturated polyol fatty acid ester stock. The enthalpy of melting of the cyclopropanated polyol fatty acid ester stock is generally less than the enthalpy of melting of the starting material or a product obtained from hydrogenation of the unsaturated polyol fatty acid ester stock by a corresponding amount (i.e., an amount which reduces the double bond content of the unsaturated polyol fatty acid ester stock by the same amount as measured by Iodine Value). In most instances, the enthalpy of melting of a cyclopropanated polyol fatty acid ester stock is reduced with respect to the pour point of the corresponding unsaturated polyol fatty acid ester stock. For example, the present method typically reduces the active methylene content of an unsaturated triacylglycerol oil by at least about 10% and preferably by at least about 25% with respect to that of the corresponding unsaturated triacylglycerol oil and at the same time decreases the enthalpy of melting of the cyclopropanated product with respect to the original polyol ester stock.

The cyclopropanating agent used to form the modified fatty acid esters is capable of adding a methylene moiety (":$CR^2R^3$") to a carbon—carbon double bond to form a cyclopropyl group. Examples of suitable cyclopropanating agent include those which are capable of adding a :$CR^2R^3$ methylene moiety to a carbon—carbon double bond, wherein $R^2$ and $R^3$ are typically independently selected from H, halo, n-alkyl, phenyl or substituted phenyl. Example of particularly suitable cyclopropanating agents are reagents which are capable of adding a hydrophobic methylene group, e.g., Simmons-Smith type reagents which are capable of adding an unsubstituted methylene moiety (":$CH_2$") or alkyl substituted methylene moiety (":CHR") to the double bond.

Lubricants including unsaturated polyol fatty acid ester stock modified to have at least one fatty acyl chain including a cyclopropyl group and processes of producing the lubricants are also provided herein. The process of producing the lubricant may also include blending the modified unsaturated ester stock with one or more petroleum based lubricating fluids and/or other additives.

DETAILED DESCRIPTION

The present method may be utilized to increase the fluidity and/or enhance the oxidative stability of unsaturated polyol fatty acid ester stocks, such as unsaturated triacylglycerol oils. For example, the method allows the production of vegetable oil based lubricants which, in addition to possessing very attractive lubricating properties, are environmentally friendly. Since unsaturated polyol fatty acid ester stock based lubricant base stocks are typically derived from natural materials, these lubricants can have low toxicity and are generally readily biodegraded.

I. Unsaturated Polyol Fatty Acid Ester Stocks

Unsaturated polyol fatty acid ester stocks include one or more unsaturated fatty acid esters and may also include one or more saturated fatty acid esters. Typically, the present unsaturated fatty acid ester stocks include a mixture of esters of saturated and unsaturated fatty acids, e.g., a mixture of saturated and unsaturated triacylglycerols such as high oleic canola oils. The stocks are made up of fatty acid esters of alcohols which include two or more hydroxy groups ("polyols" or "polyhydric alcohols"). Fatty acid esters which are formed from polyhydric alcohols typically have all of the hydroxy groups esterified. Such esters include at least two fatty acyl chains and preferably one fatty acyl chain per hydroxy group. Esters in which a portion of the hydroxy groups are esterified with a short chain carboxylic acid (i.e., carboxylic acids such as acetic and propionic acid which contain no more than 5 carbon atoms) are also included within the present definition of fatty acid esters. Typically no more than about 5 wt. % of the corresponding fatty acid composition and preferably much less is made up of short chain carboxylic acid(s). Preferably, all but one and, more preferably, all of the hydroxy groups of the alcohol portion of the esters are esterified to a fatty acyl group. As employed herein, the term "fatty acyl group" refers to acyl groups ("—C(O)R") which include an aliphatic chain (linear or branched) typically having from about 6 to about 30 carbon atoms.

Polyols which can be used to form the present unsaturated fatty acid esters include at least two and, preferably, at least three hydroxy groups per molecule. Typically, the polyols have no more than about 6 hydroxy groups per alcohol molecule and include up to about 20 carbon atoms and preferably no more than about 8 carbon atoms. Examples of suitable aliphatic polyols include glycerol, alkylene glycols (e.g., ethylene glycol, diethylene glycol, triethylene glycol and neopentylglycol), pentaerythritol, trimethylolethane, trimethylolpropane, and sorbitol. Suitable alicyclic polyols include cyclohexanediols and inositol as well as natural cyclic polyols such as glucose, galactose and sorbose.

Fatty acid esters of polyols which include no more than about 6 carbon atoms and have three to six hydroxy groups per molecule, such as glycerol, pentaerythritol, trimethylolethane, trimethylolpropane, sorbitol, inositol, glucose, galactose, and/or sorbose, are particularly suitable for use in the present invention. Preferably, such esters have a fatty acid composition which includes at least about 90 wt. % fatty acyl groups with aliphatic chains having from about 16 to 20 carbon atoms. More preferably, the unsaturated fatty acid ester stocks employed in the present invention have an Iodine Value of no more than about 130 and are modified to have an average cyclopropyl content of at least about 0.25 cyclopropyl groups per fatty acyl chain.

Unlike petroleum-based lubricants, polyol fatty acid esters, such as triacylglycerols, have slight polarity on one end of the molecule due to the presence of the ester linkages. In some instances, this can be desirable when the material is used as a lubricating fluid, since the polar end of triacylglycerol molecules can become attracted to a metallic surface, while the nonpolar hydrocarbon region will generally project outwardly from metallic surfaces. This causes, in some instances, molecular attraction and alignment, and can result in better boundary lubrication with increased load carrying capacity and reduction in wear.

While the unsaturated fatty acid ester stocks employed in the present invention typically include fatty acid esters of polyhydric alcohols, for some applications, the unsaturated stock may be primarily made up of fatty acid esters of monohydric alcohols ("monoesters"). For example, fatty acid monoester stocks may be used as a fuel with enhanced lubrication properties in comparison to conventional petroleum fuels. For such applications, the esters typically include an acyl chain having from 10 to 24 and, preferably from 16 to 22 carbon atoms. The alcohol portion of the ester molecules generally includes no more than about four carbon atoms and preferably is a methyl or ethyl ester.

II. Properties of Unsaturated Triacylglycerol Oils

Unsaturated triacylglycerol oils include triacylglycerol molecules (sometimes termed triglycerides). In general, triacylglycerols comprise three long fatty acid chains esterified to glycerol; or, alternatively phrased, glycerol esterified by addition thereto of three long chain fatty acids. Herein, the terms "triacylglycerols" and "triglycerides" are intended to be interchangeable, and will in some instances be referred to by the abbreviation "TAG".

As indicated above, any given triacylglycerol molecule generally includes glycerol esterified with three fatty acid molecules. Thus, each triacylglycerol includes three fatty acid residues. In general, oils extracted from any given plant or animal source comprise a mixture of triacylglycerols, characteristic of the specific source. The mixture of fatty acids isolated from complete hydrolysis of the triacylglycerols in a specific source are generally referred to as a "fatty acid composition". By the term "fatty acid composition" reference is made to the identifiable fatty acid residues in the various triacylglycerols. The distribution of specific identifiable fatty acids is typically characterized by the amounts of the individual fatty acids as a weight percent of the total mixture of fatty acids obtained from hydrolysis of the particular oil stock.

For example, the fatty acid composition of CV-75, a typical high oleic canola oil is as shown in Table I below.

TABLE I

Fatty Acid Composition of
Typical High Oleic Canola Oil

| Fatty acid | Weight Percent[1] |
|---|---|
| Palmitic acid | 4.0 |
| Stearic acid | 3.0 |
| Oleic acid | 74.0 |
| Linoleic acid | 11.5 |
| Linolenic acid | 4.5 |
| Other | 3.0 |

[1]Weight percent of total fatty acid mixture derived from hydrolysis of CV-75.

Palmitic and stearic acids are saturated fatty acids and triacylglycerol acyl chains formed by the esterification of either of these acids do not contain any carbon—carbon double bonds. However, many fatty acids such as oleic acid, linoleic acid and linolenic acid are unsaturated. Oleic acid is an 18 carbon fatty acid with a single double bond; linoleic acid is an 18 carbon fatty acid with two double bonds or points of unsaturation; and linolenic is an 18 carbon fatty acid with three double bonds. More specifically, oleic acid is (Z)-9-octadecenoic acid;

linoleic acid is (Z,Z)-9,12-octadecadienoic acid;

alpha-linolenic acid is (Z,Z,Z)-9,12,15-octadecatrienoic acid; and gamma-linolenic acid is the (Z,Z,Z)-6,9,12 isomer of octadecatrienoic acid.

The average number of double bonds present per fatty acyl chain in an unsaturated polyol fatty acid ester is referred to herein as the "average unsaturation content." For example, the average unsaturation content of an unsaturated triacylglycerol oil may be calculated based from the distribution of fatty acids in the mixture produced by hydrolysis of the triacylglycerols. The distribution of fatty acids in a particular oil may be readily determined by methods known to those skilled in the art. Unsaturated triacylglycerol oils which are particularly suitable for use as starting materials in the present methods generally have an average unsaturation content of no more than about 1.7 and, preferably, about 0.4 to about 1.3 per fatty acyl chain.

As an example, on average, each triacylglycerol molecule in CV-75 contains about 3.3 double bonds, distributed among the various fatty acyl chains (three chains in each triacylglycerol molecule), i.e., CV-75 has an average unsaturation content of about 1.1 per acyl chain. This results from the fact that CV-75 includes a mixture of triacylglycerols and the triacylglycerol molecules of CV-75 generally each have a mixture of fatty acid residues.

Another measure for characterizing the average number of double bonds present in a polyol fatty acid ester stock (such as the triacylglycerol molecules of an unsaturated triacylglycerol oil) is its Iodine Value. The Iodine Value of a triacylglycerol or mixture of triacylglycerols is determined by the Wijs method (A.O.C.S. Cd 1-25). The present method can be used to improve the fluidity and oxidative stability of unsaturated triacylglycerol oils having a wide range of Iodine Values. Typically, however, the present methods employ as starting materials unsaturated polyol fatty acid ester stocks, such as vegetable oil stocks, having an Iodine Value of no more than about 150, preferably about 70 to about 140, and, more preferably, about 80 to about 110.

For example, high oleic canola oil typically has an Iodine Value of about 85 to about 110 and a pour point of about −10° C. to −15° C. Hydrogenation of such oils to reduce its Iodine Value to about 75 or less can improve the oxidative stability of the oil. Hydrogenated oils with this level of Iodine Value, however, generally have substantially decreased fluidity as evidenced by an increase in pour point to about 10 to 30° C. or higher and can become solids at room temperature thereby limiting their use as a functional fluid.

During use and/or storage lubricants tend to break down due to oxidation or other degradation processes. When employed as a functional fluid, such as a lubricating fluid, a vegetable oil may oxidize during which polymerization and degradation occurs. Polymerization increases viscosity and reduces lubrication functionality. Degradation leads to breakdown products that may be volatile or corrosive. In either case, undesirable modifications to the lubricating characteristics of the fluid occur.

One measure of the oxidative stability of a polyol fatty acid ester stock is the effect on viscosity observed after passing an oxygen-containing gas through a heated sample of the oil stock. For example, the viscosity of a sample may be measured after passing a controlled flow of air through a sample of oil heated to 110° C. according to the procedure described in A.O.C.S. Method Cd 12b-92. The relative stability of the sample can be characterized in a number of ways, e.g., the amount of time required to achieve a specified increase in viscosity or by measuring the change in viscosity after passing air through the heated sample form a designated period of time. The term "Oxidized Viscosity Index" ("OVI") as used herein refers to the amount of time required to produce an 500 cP increase in viscosity in a sample which has been treated under the conditions described in A.O.C.S. Method Cd 12b-92. For example, the present fatty acid ester stocks generally have an OVI of at least about 50 hours, and more preferably of at least about 100 hours.

The term "$OV_x$" is used herein to refer to the viscosity of a sample treated under the oxygenation conditions described in A.O.C.S. Method Cd 12b-92 for a preset length of time ("X" in hours). Thus, "$OV_{50}$" refers to the viscosity of a sample after passing air through a 110° C. sample at about 140–150 mL/min for 50 hours. Preferably, the cyclopropanated products of the present invention have an $OV_{50}$ of no more than about 500 cP and, more preferably, no more than about 300 cP.

The conditions of lubricating fluid storage and/or use, which may involve exposure to substantial heat; pressure; metal surfaces, etc., can facilitate the oxidation process. It is desirable, then, to use lubricating fluids which are not readily susceptible to undesirable levels of oxidation and/or polymerization, at least under normal storage and use conditions. Unsaturated fatty acyl chains are more readily susceptible to oxidation than saturated fatty acyl chains. Thus, triacylglycerols such as those found in vegetable oils, which contain substantial amounts of oleic acid, linoleic acid and/or linolenic acid residues, can be subject to undesirable levels of oxidation and/or polymerization.

The undesirable levels of oxidative instability are presently believed to be due in large part to the presence of polyunsaturated fatty acyl chains that contain "active methylene groups." As used herein, active methylene groups refers to —$CH_2$— groups which are situated between two double bonds in a fatty acyl chain, i.e., doubly allylic —$CH_2$— groups. When found, the active methylene groups are typically present in dienic and trienic polyunsaturated fatty acyl chairs. Active methylene groups are principally present in polyunsaturated fatty acid-containing triacylglycerol molecules, e.g., linoleic esters (with one active methylene group) and linolenic esters (with two active methylene groups). The term "active methylene content" as used herein refers to the average number of active methylene groups per fatty acyl chain in a polyol fatty acid ester such as an unsaturated triacylglycerol oil. The active methylene content of an unsaturated triacylglycerol oil can be calculated based from the fatty acid composition of the unsaturated triacylglycerol oil. For example, it can be calculated based on the fatty acid composition listed in Table I that CV-75 contains an average of about 0.2 active methylene groups per fatty acyl chain.

It has been found that the oxidative stability, particularly as it relates to lubricating applications, of an unsaturated polyol fatty acid ester stock is substantially enhanced if the cyclopropanated stock has an active methylene content of no more than about 0.5, preferably no more than about 0.3 and, more preferably, no more than about 0.1. For example, cyclopropanation of vegetable oil to reduce its active methylene content to no more than about 0.3 can enhance the oxidative stability of the cyclopropanated adduct with respect to the original stock.

Of course, the propensity for a triacylglycerol to oxidize can also be reduced by hydrogenation of the double bond(s). That is, as the extent of hydrogenation increases (and the Iodine Value and active methylene content decrease), the propensity toward oxidation decreases. Unfortunately, however, hydrogenation generally is accompanied by concomitant, and undesirable, increase in "pour point", i.e., reduction in the fluidity of the oil. For example, a saturated triacylglycerol, tristearin (the stearic acid triester of glycerol; stearic acid is octadecanoic acid; $C_{18}H_{36}O_2$), has a melting point of 74° C., compared to melting points of 5° C. triolein and −11° C. for trilinolein.

It is apparent, then, that one cannot simply hydrogenate an unsaturated triacylglycerol oil such as vegetable oil to obtain an oxidatively stable lubricating fluid. Thus, although vegetable oils exhibit many properties desirable in a lubricating fluid, such oils have generally not been acceptable due to propensity toward oxidation and the resulting increase in viscosity, and if hydrogenated, undesirable levels of loss of fluidity (or increase of pour point).

In general, similar affects are observed with a variety of vegetable oils. For example, palm oil, which has a low average unsaturation content (e.g., an Iodine Value of about 40 to 60), is a semi-solid at room temperature and is generally not useful as a lubricant despite its relatively good oxidative stability. On the other hand, linseed oil, which has a very high level of polyunsaturation (fatty acyl groups containing more then one double bond) and an Iodine Value of 170 to 180, has a low pour point due to the propensity of the polyunsaturated fatty acyl chains to crosslink and/or polymerize. Due to the propensity of linseed oil to crosslink or polymerize, unsaturated triacylglycerol oils used to produce a lubricant base stock by the present methods typically do not include a significant amount of linseed oil, e.g., less than about 25 wt. %, preferably no more than about 10 wt. %, and most preferably are substantially free (i.e., less than about 0.1 wt. %) of linseed oil.

Because of the tendency of unsaturated fatty acid esters stocks having very high levels of polyunsaturation to polymerize, plant or animal derived oil stocks having an active methylene content of no more than about 1.0 and/or an Iodine Value of no more than about 150 are typically used to produce lubricant base stocks using the present method. Preferably, the starting unsaturated triacylglycerol oil has an active methylene content of no more than about 0.8, preferably no more than about 0.65 and/or includes no more than about 15 wt. % (on a fatty acid composition basis), preferably no more than about 10 wt. % of trienic (i.e., having three double bonds) unsaturated fatty ester groups, such as esters of linolenic acid.

III. Modifications to Unsaturated Polyol Fatty Acid Ester Stocks for Use as Lubricating Fluids

A. General.

The fluidity of a material is in part determined by the ability of molecular packing, intermolecular interactions, and molecular weight. In general, increasing branching of a hydrocarbon, especially towards the methyl end, or introducing unsaturation in the chain increases fluidity since it disrupts packing. By "increase in fluidity" in this context, reference is meant to reduction in "pour point" or "melting point". The term "pour point" as used herein refers to the temperature at which the material stops flowing (as measured by ASTM method D 97). Thus pour point is a property which may involve a phase change but generally is based on a change in the viscosity properties of the material. The term "melting point" as used herein refers to the temperature at which a material transforms from a solid to a liquid, i.e., when a phase change involving a heat of fusion occurs.

In addition to pour point, the viscosity of an unsaturated polyol fatty acid ester stock (such as an unsaturated triacylglycerol oil or modified version thereof) at room temperature or an elevated temperature (e.g., 40° C.) may be used to characterize its fluidity. Unless otherwise indicated, viscosities reported herein are in centipoise (cP) as determined using a Brookfield viscometer type R. V. F. at a 20 rpm setting. The present cyclopropanated products typically have a viscosity at 40° C. of no more than about 200 cP and, preferably, no more than about 100 cP.

Introducing cis unsaturation into a fatty acyl chain typically produces a greater increase in fluidity than the introduction of a trans double bond since it disrupts packing to a greater extent. One advantage of the present method, is that the majority of cyclopropanation reagents add a methylene moiety to a carbon—carbon double bond in a manner that preserves the stereochemistry of the double bond, i.e., a cis disubstituted double bond is generally converted into a cis disubstituted cyclopropyl group. This is extremely advantageous since the majority of double bonds in naturally occurring fatty acyl chains have a cis configuration. Thus, the present method removes a double bond from a fatty acyl chain, thereby decreasing the propensity of the fatty acyl group towards oxidation and/or polymerization, while preserving the advantageous effect of a cis configuration ("kinking effect") on fluidity properties. The enthalpy of melting of a sample is indicative of the amount of energy necessary to transform the sample from a solid to a liquid. A decrease in enthalpy of melting provides a good indication that the sample has been modified to have less ordered packing. The present cyclopropanated products typically have an enthalpy of melting which is at least about 10 J/g and, preferably, at least about 50 J/g lower than that of the unsaturated polyol fatty acid ester stock.

For some lubricants, the desired fluidity properties may be specified in terms of a viscosity index (as determined by ASTM method D 2270). For example, it is characteristic of triacylglycerol oils that their viscosity fluctuations as a function of temperature change to a lesser extent than the viscosities of petroleum based mineral oils. The viscosity-to-temperature properties of each oil can be characterized in terms of the viscosity index ("VI"). A higher viscosity index signifies that the viscosity of the oil concerned changes less as a function of changes in temperature. The viscosity indexes of triacylglycerols (typically in the range of about 180 to about 225) are clearly higher than those of petroleum based mineral oils with no additives (typically 50–120), so that triacylglycerols are to their nature so-called multigrade oils. This is of considerable importance under conditions in which the operating temperature may vary within rather wide limits. Modified unsaturated triacylglycerol oils produced by the present methods generally have a viscosity index which is quite similar to the original triacylglycerol oil. Preferably, the present modified unsaturated triacylglycerol oils have a viscosity index of at least about 130 and, more preferably, at least about 140. This is typically achieved by selecting a starting unsaturated triacylglycerol oil which has close to the viscosity index desired for the modified product.

As part of the development of the present techniques, it was theorized that triacylglycerols having therein substantial sites of unsaturation could be improved, with respect to fluidity, by generation of cyclopropyl groups, i.e., moieties extending from at least some of the long acyl chains. It was foreseen that such cyclopropyl groups would limit the ability for the fatty acyl chains to pack closely. At the same time, a cyclopropyl group generated via a cyclopropanation reaction would remove a double bond from the acyl chain backbone. This can create at least two benefits: (i) a decrease in the possibility of double bond migration to generate a less stable polyunsaturated chain, e.g., through the formation of a conjugated diene or triene fatty acyl chain; and (ii) decrease the possibility of volatile degradation products being generated through oxidative cleavage. In addition, as mentioned above, the cyclopropanation reaction generally preserves a cis configuration present in the original double bond and the associated "kinking effect." Thus, it was theorized that through cyclopropanation, a desirable lubricating fluid could result which would possess appropriate characteristics with respect to both stability towards oxidation and, desirably, low pour point or melting point.

B. Cyclopropanated Adducts

Modification of unsaturated triacylglycerol oils through formation of a cyclopropanated product can increase the oxidative stability with respect to the unmodified vegetable oil stock, e.g., increase the "Oxidized Viscosity Index" ("OVI") by at least about 50%. Preferably, the formation of a cyclopropanated product can be used to increase the OVI of an unsaturated polyol fatty acid ester by a factor of at least about 2 (i.e., increased by at least about 100%) with respect to the corresponding unmodified unsaturated polyol fatty acid ester.

It has been found that cyclopropanation may be used to modify unsaturated polyol fatty acid ester, such as triacylglycerol oils, to improve their properties as lubricating fluids. It can be theorized that when a cyclopropanating agent, such as a Simmons-Smith reagent, is reacted with polyol fatty acid ester having an unsaturation therein, a methylene moiety is added to a carbon—carbon double bond or point of unsaturation in the unsaturated ester stock reacts to form a cyclopropyl group.

The modified polyol esters of the present invention may be produced by reacting a cyclopropanating agent with at least a portion of the carbon—carbon double bonds of an unsaturated polyol fatty acid ester stock. The cyclopropanating agent is capable of reacting with the double bond to add a methylene moiety (":$CR^2R^3$") and produce a cyclopropyl group. Depending on the nature of the cyclopropanating agent, the methylene moiety may be unsubstituted (i.e., :$CH_2$) or may be substituted with one or two substituents. While a wide variety of cyclopropanating agents are known to those skilled in the art, the cyclopropanating agent is preferably capable of reacting with the double bond to produce a hydrophobic cyclopropyl group. In addition to an unsubstituted methylene moiety, examples of of suitable cyclopropyl groups include those substituted with halogen, alkyl and/or phenyl (optionally substituted with one or more common substituents such as halogen, lower alkoxy, lower alkyl, cyano, carboxyalkyl and/or haloalkyl). Preferably, the cyclopropanating agent is capable of adding a :$CR^2R^3$ methylene moiety to form the cyclopropyl group where $R^2$ and $R^3$ are independently selected from H, F, Cl or Br. Most preferably, the cyclopropanating agent is capable of adding :$CH_2$, :$CCl_2$ and/or :$CBr_2$ to a carbon—carbon double bond to form a cyclopropyl group.

One suitable class of cyclopropanating agent are those which are capable of adding a :$CH_2$ methylene moiety to the double bond via a Simmons-Smith type reaction. Such cyclopropanating agents typically include zinc reagent and a dihalomethane, e.g., R'CHXY where X is bromo or iodo, Y is chloro, bromo or iodo, and R' is hydrogen or alkyl, more preferably, n-C(1–6)alkyl. Particularly suitable dihalomethanes for use in the Simmons-Smith type reaction include $CH_2Br_2$ and $CH_2I_2$. The zinc reagent typically includes zinc-copper couple ("Zn(Cu)"), zinc-silver couple ("Zn(Ag)"), or dialkyl zinc (e.g., diethyl zinc).

a single "methylene moiety" to an unsaturated triacylglycerol oil. It is expected that reaction between the cyclopropanating agent and an unsaturated triacyglycerol could occur at one or more of a number of positions along a fatty acyl chain. The reaction may also occur with double bonds on one or more of the fatty acyl chains within a triacylglycerol molecule. By way of illustration, a cyclopropanation reaction of vegetable oil to produce a cyclopropanated product can be carried out by a variety of methods such as those described in Simmons et al., "Organic Reactions," vol. 20, pp. 1–131 (1973) and March, "Advanced Organic Chemistry," 3rd edition, John Wiley & Sons, New York, N.Y., pp. 170–176, 768–771 (1985).

The cyclopropanation reaction, it is believed, has at least two beneficial affects. First, it helps to reduce the susceptability of the unsaturated triacylglycerol oil to oxidation. In addition, the presence of the resulting cyclopropyl groups in the fatty acyl chains appears to decrease the ease of packing and thus helps to maintain a low pour point or melting point.

It is important to recognize that in commercial practice of the techniques described herein, the techniques will typically be operated on mixtures of triacylglycerols either isolated as a plant or animal oil, e.g., by various oil seeds Scheme 1

As illustrated in Scheme 1, a cyclopropanating agent can react with a double bond in one of the fatty acyl chains of a triacylglycerol. The reaction may occur at a double bond in either a fatty acyl chain esterified at a primary hydroxyl group of the glycerol (e.g., the :$CH_2$ adduct shown in Scheme 1) or in a fatty acyl chain esterified at a secondary hydroxyl group of the glycerol (e.g., the :$CX_2$ adduct shown in Scheme 1). The formation of a cyclopropyl groups lowers the Iodine Value or average unsaturation content of the unsaturated triacylglycerol oil by removing a point of unsaturation, i.e., the number of double bonds present per triacylglycerol molecule is decreased by the cyclopropanation reaction. In addition, the number of active methylene groups present can be reduced by cyclopropanation of a polyunsaturated acyl chain of a polyol fatty acid ester. For example, the reaction of a Simmons-Smith reagent with the C12-double bond of a linoleic ester chain as shown in Scheme 1, destroys the allylic character of the methylene group at the 11 position. Moreover, as discussed herein, it is believed that the cyclopropanation introduces bulk onto acyl chains of triacylglycerols and leads to a cyclopropanated product having a lower enthalpy of melting.

As illustrated in Scheme 1, there are a variety of cyclopropanated adducts that can be formed from the addition of processing techniques, or resulting from alteration of such oils, for example by prior partial hydrogenation.

Herein, when it is said that the "unsaturated polyol fatty acid ester stock" or "unsaturated triacylglycerol oil" contains an average of at least one double bond per triacylglycerol (or triacylglycerol) molecule therein ("unsaturation content"), reference is meant to the average double bond presence in the triacylglycerol mixture, on a per fatty acid chain basis. An unmodified high oleic canola oil, as indicated above, generally contains an average of about 3.3 double bonds per molecule and about 1.1 double bonds per acyl chain. Examples of other unmodified vegetable oils and fish oils include those listed in Table II below (together with typical Iodine Values for the oils). Of course, the "unsaturated triacylglycerol oil" is employed in applications according to the present invention may comprise a mixture of oils from a variety of sources.

TABLE II

| Unsaturated Triacylglycerol Oil | Iodine Value |
| --- | --- |
| Rapeseed oil | 97–108 |
| Corn oil | 103–128 |
| Peanut oil | 84–100 |
| Safflower oil | 140–150 |
| Olive Oil | 80–88 |
| Soybean oil | 120–130 |
| Sunflower oil | 125–136 |
| Cottonseed oil | 99–113 |
| Menhaden oil | 150–160 |
| Herring oil | 115–160 |

Herein, in connection with cyclopropanation of the unsaturated fatty acid ester stock, reference will in some instances be made to "at least partially cyclopropanating". By this, it is meant that the starting unsaturated polyol ester stock is treated under appropriate conditions to add a methylene group to at least some of the double bonds to form cyclopropyl groups. In order to be considered "at least partially cyclopropanated" as the term is used herein, there should be a reduction of at least 10%, and preferably at least about 25% of the total number of double bonds (on an average per molecule basis for the whole cyclopropanated product). The term "on an average per molecule basis" in this connection, is meant to refer to on an average per total of triacylglycerol molecules in the reaction mixture, whether those molecules includes a cyclopropyl group or are an unreacted triacylglycerol molecule.

From the above, it will be understood that the intent is to reference techniques that may be practiced on mixtures, without precise analysis of exact adduct and unreacted triacylglycerol presence in the mixture, but rather with a general understanding of overall cyclopropanation during modification. The intent, in general, is to obtain a stock of desirable property with respect to, inter alia, pour point and stability. Indeed, it is foreseen that in some applications blends may well be desirable, depending on the use to which the lubricating stock is to be placed. The present method is particularly useful for producing lubricant base stocks which include a predominant amount of a modified unsaturated triacylglycerol oil, e.g., a lubricant base stock including at least about 50 wt. % and, preferably, at least about 75 wt. % of the modified unsaturated triacylglycerol oil. By employing the present method, biodegradable, triacylglycerol oil-based base stocks which have a combination of oxidative stability and viscosity properties suitable for a variety of lubricant applications may be produced. Preferred embodiments of the invention include such base stocks having an oxidative stability characterized by an OVI of at least about 50 hours, preferably at least about 100 hours, and/or an active methylene content of no more than about 1.5 and, preferably, no more than about 1.0. Preferred base stocks typically fluid at room temperature and have a viscosity index of at least about 125 and a viscosity at 40° C. of no more than about 200 cP and, preferably, no more than about 125 cP.

1. Some Preferred Vegetable Oils.

Techniques according to the present invention, as will be understood from the experimental report below, were particularly developed for generation of desirable lubricating fluids from vegetable oils. In general, this is because of the particular level of unsaturation found in many vegetable oils, as well as the physical properties both of starting materials and the final adducts. In general, improvement is observed if the extent of cyclopropanation is such that at least about 0.5 cyclopropyl groups are added per triacylglycerol molecule, on average. Generally, reactions to the extent of 0.7 to 1.5 cyclopropyl groups added, per triacylglycerol molecule, will be preferred. This can readily be controlled by judicious choice of the starting vegetable oil stock, the type and amount of cyclopropanation agent employed and the reaction conditions. More broadly, improvement in the oxidative stability of an unsaturated polyol ester stock, such as a vegetable oil stock, can be produced through the addition of at least about 0.25 cyclopropyl groups on average per triacylglycerol molecule. It has been found that the cycloaddition up to about 2.0 cyclopropyl groups on average per triacylglycerol molecule can generally produce a substantial enhancement in the oxidative stability of the unsaturated triacylglycerol oil.

Particularly suitable vegetable oils for use with the present method include high oleic oils, i.e., oils which have a fatty acid composition containing at least about 50 wt. % oleic acid. Other vegetable oils which, it is foreseen, may be modified with techniques according to the present invention, include: rapeseed oil, olive oil, sunflower oil, soybean oil, safflower oil, peanut oil, cottonseed oil, crambe oil, mustard oil, and meadowfarm oil. As used herein, "rapeseed oil" includes high erucic acid rapeseed oil ("HEAR") and low erucic acid rapeseed oil ("LEAR" or canola oil). Variants of some of the other oils listed above are also known, e.g., high oleic and very high oleic sunflower and canola oils. As discussed herein, these vegetable oils may be employed in the present invention as isolated or in altered form, as well as with oil from a single source or mixtures of one or more of the types of oils (or altered forms thereof).

IV. Some Preferred Products

A. A Lubricating Fluid Base.

Techniques according to the present invention can be utilized to prepare preferred lubricating fluid bases, or base stocks, from various plant or animal oils. As indicated above, a vegetable oil derivative can be prepared, for example, as a lubricating base stock. Lubricating base stocks would, in general, be fluids that can be used as the ingredient present in the highest amount by weight in a wide variety of lubricating fluids, for example, as the base fluid stock for crankcase oils, transmission oils, power transfer fluids (e.g., hydraulic fluids), gear oils and greases. It is foreseen that such materials may be used as the lubricating fluid base in such industries as: the automotive industry, metalworking and metal forming industries, earth moving industry, and general manufacturing.

B. Preparation of Lubricating Fluids from the Base Stock.

The major constituent of a lubrication fluid is a base oil (base stock) formulated with small amounts of additives. The base oil provides the primary lubricant functionality and performance. The additives enhance the performance of the base oil and also provide additional advantages and/or remove the shortcomings of the base oil.

Once base stocks according to the present invention are developed, they can be readily converted into lubricating fluid by the provision therein of appropriate additives. For example, to make lubricants, such as motor oils, transmission fluids, gear oils, industrial lubrication oils, metal working oils, and the like, one typically starts with a lubricant grade of the present modified unsaturated polyol fatty acid ester stock (also referred to collectively herein as a "cyclopropanated base stock"). Into this "base stock" is typically blended a small amount of specialty chemicals that can enhance lubricity, inhibit wear and corrosion of metals, and retard damage to the fluid from heat and oxidation.

As previously indicated, the modified polyol esters of the present invention are useful in preparing lubricants, particularly lubricants based on synthetic lubricating oils and mixtures thereof. The compositions of the invention can be employed in a variety of lubricants based on diverse oils of lubricating viscosity, including natural and other synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. The lubricants can also be used in natural gas engines, stationary power engines and turbines and the like. Automatic or manual transmission fluids, transaxle lubricants, gear lubricants, both for open and enclosed systems, tractor lubricants, metal-working lubricants, hydraulic fluids and other lubricating oil and grease compositions also can be prepared with compositions of the present invention. The polyester polyols may also be used in lubricants for wirerope, walking cam, slideway, rock drill, chain and conveyor belt, worm gear, bearing, and rail and flange applications.

The lubricating oil compositions of the present invention include modified unsaturated polyol ester as described herein and, in addition, typically include at least one other oil of lubricating viscosity which is different from the ester (A). Typical lubricating oil compositions of the invention include about 10 to about 95 wt. % of the polyol ester (A) and about 0.5 to about 90 wt. % of an oil of lubricating viscosity other than the ester (A). Such lubricating oil compositions also may, and preferably, contain antioxidant and other performance additives as described herein. The amount of the antioxidant and other performance additives included in the lubricating oil composition typically ranges from about 0.01% to about 10% more often from about 0.1% to about 7% or 8%. The amount of the antioxidant in other performance additives included in the lubricating oil compositions will depend on the use for which the lubricant is designed, and such amounts can be readily determined by those skilled in the art.

The lubricating compositions and methods of this invention employ an oil of lubricating viscosity other than the polyol esters (A) described above, and such oils include natural or synthetic lubricating oils and mixtures thereof. Natural oils include animal oils, vegetable oils (including high oleic vegetable oils), products derived from vegetable oils (e.g., rapeseed oil reacted with methanol in the presence of a catalyst forms a rapeseed methyl ester), mineral lubricating oils, solvent or acid treated mineral oils, hydrorefined mineral oil and hydrocracked mineral oils. Synthetic lubricating oils include hydrocarbon oils (poly-alpha-olefins), halo-substituted hydrocarbon oils, alkylene oxide polymers, esters of mono- and dicarboxylic acids and polyols, esters of phosphorus-containing acids, polymeric tetrahydrofurans and silicon-based oils. Unrefined, refined, and rerefined oils, either natural or synthetic, may be used in the compositions of the present invention. A description of oils of lubricating viscosity occurs in U.S. Pat. No. 4,582,618 (column 2, line 37 through column 3, line 63, inclusive), herein incorporated by reference for its disclosure to oils of lubricating viscosity.

In one embodiment, the lubricating compositions can have an SAE gear viscosity number of at least about SAE 65, more preferably at least about SAE 75. The lubricating composition may also have a so-called multigrade rating such as SAE 75W–80, 75W–90, or 80W–90. Multigrade lubricants may include a viscosity improver which is formulated with the oil of lubricating viscosity to provide the above lubricant grades.

In another embodiment, the oil of lubricating viscosity is selected to provide lubricating compositions for crankcase applications, such as for gasoline and diesel engines. Typically, the lubricating compositions are selected to provide an SAE crankcase viscosity number of 10W, 20W, or 30W lubricants. The lubricating composition may also have a so-called multi-grade rating such as SAE 5W–30, 10W–30, 10W–40, 20W–50, etc. As described above, multi grade lubricants can include a viscosity improver which is formulated with the oil of lubricating viscosity to provide the above lubricant grades.

Other Lubricant Components

The compositions of this invention, and particularly, the lubricating oils, functional fluids, and greases of the invention may contain performance additives, such as antioxidants, detergents, dispersants, metal deactivators, antiwear agents, extreme-pressure agents, viscosity index modifiers, pour point depressants, foam inhibitors, demulsifiers, friction-modifiers, and/or corrosion-inhibitors. Some of the antioxidants described above also function as antiwear agents, extreme-pressure agents, or corrosion-inhibitors, but supplemental antiwear agents, extreme-pressure agents and corrosion-inhibitors often are desirable in the compositions of the invention.

A wide variety of antioxidant compositions can be used in combination with the polyol esters of the invention. Examples of various types of antioxidants which can be used in combination with the polyol esters include sulfur-containing compositions, aromatic amines including alkylated aromatic amines, phenols, oil-soluble transition metal containing compounds, etc. More particularly, the antioxidants useful in the present invention may be selected from phenolics, aromatic amines, phenothiazines, dithiophosphates, dithiocarbamates, sulfides, sulfurized olefins, sulfurized oils including vegetable oils, sulfurized fatty acids or esters, sulfurized Diels-Alder adducts, and tocopherols.

Small amounts of antioxidants can interact with the polyol ester stocks of the present invention to provide stabilized polyol ester stocks. Generally, the polyol esters can be stabilized with up to 5% by weight, based on the weight of the polyester of one or more antioxidants and more often, amounts of 3% or less of antioxidant is effective in significantly improving the stability of the polyol esters.

Metal deactivators which may be included in the present lubricant compositions generally include triazole-containing compound(s) and more particularly, benzotriazole and/or substituted benzotriazole(s). A wide variety of aromatic triazoles are known, many of which are described in detail in "Benzotriazole: A Novel Synthetic Auxiliary," Katritsky, Rachwal and Hitchings, Tetrahedron, Vol. 27, No. 16/17, p. 2683–2732, 1991 (Pergamon Press plc), along with methods for their preparation.

Suitable detergents for use in the present compositions are exemplified by oil-soluble neutral and basic salts (i.e. overbased salts) of alkali, alkaline earth, or transition metals with sulfonic acids, carboxylic acids, including hydrocarbyl substituted carboxylic acylating agents, phenols or organic phosphorus acids. The hydrocarbyl-substituted carboxylic acylating agents include agents which have a hydrocarbyl group derived from a polyalkene, such as polybutene. The polyalkenes can include homopolymers and interpolymers derived from one or more olefins. The polyalkene is generally characterized as containing from about 8 up to about 300 carbon atoms. In one embodiment, the polyalkene is typically characterized by an Mn (number average molecular weight) of about 500 to about 5000.

Suitable antiwear, extreme-pressure, friction modifiers and corrosion-inhibiting agents include chlorinated aliphatic hydrocarbons, such as chlorinated wax; alkyl-substituted succinic acids or anhydrides reacted with alkylene oxides such as ethylene oxide or propylene oxide; sulfurized alkylphenols; phosphosulfurized hydrocarbons, such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; boron-containing compounds including borate esters; dimercaptothiadiazole derivatives; amino-mercaptothiadiazole derivatives; and molybdenum compounds. Many of the above-mentioned antioxidants can also serve as extreme-pressure agents and corrosion-inhibitors.

Pour point depressants are an additive which is also often included in the lubricating oils described herein. Examples of useful pour point depressants are polymethacrylates; polyacrylates; polyacrylamides; condensation products of haloparaffin waxes and aromatic compounds; minerol oils; fatty acid alkyl esters; petroleum based hydrocarbons; vinyl carboxylate polymers; styrene-maleic anhydride copolymer esters; and polymers of dialkylfumarates, vinyl esters of fatty acids and alkyl vinyl ethers.

Antifoam agents are used to reduce or prevent the formation of stable foam. Typical antifoam agents include silicones or organic polymers. Additional antifoam compositions are described in "Foam Control Agents," by Henry T. Kerner (Noyes Data Corporation, 1976), pages 125–162.

Suitable viscosity improvers include but are not limited to polyolefins, such as ethylene-propylene copolymers, polyisobutenes, or polybutylene; rubbers, including hydrogenated rubbers, such as styrene-butadiene or styrene-isoprene rubbers; polyacrylates, including polymethacrylate acid esters and polyacrylate acid esters; diene polymers, polyalkyl styrenes, alkenyl aryl conjugated diene copolymers (preferably styrene-maleic anhydride copolymer esters), hydrogenated isoprenoids and multifunctional viscosity improvers. Particularly suitable viscosity improvers include polyolefin or polymethacrylate. Commercially available viscosity improvers include Acryloid(tm) viscosity improvers available from Rohm & Haas; Shellvis(tm) rubbers available from Shell Chemical; hydrogenated polyisoprenoids from Kurary Co.; and Lubrizol 3174 available from The Lubrizol Corporation.

The amount and type of additives required in a formulation depends upon the severity of the application; usually the additives vary from 5 to 20% of the total formulation. Types of additives that commonly used in lubricant formulations include: viscosity index improvers (e.g., a few % polyisobutylenes and/or polymethacrylates); oxidation inhibitors (e.g., 0.5–1.0% di-tert-butyl-p-cresol and/or other phenolic antioxidant); pour point depressants (e.g., circa 1% of a polymethacrylate); antiwear agents (e.g., a few % of a polar fatty acid compound and/or a zincdiorganodithiophosphate); detergent dispersants (e.g., 2–20% of a sulfonate and/or a phosphate); and rust inhibitors (e.g., circa 1% of a mildly polar organic acids, organic phosphates and/or amines).

IV. Illustrative Experimental Examples

Example 1—Cyclopropanation of Trioleoylglycerol

To a suspension of 100 g of freshly prepared zinc-copper couple (III) in dry diethyl ether (500 mL) stirred mechanically under reflux was added dropwise a solution of 130 g of trioleoylglycerol and 433 g of diiodomethane in dry diethyl ether (100 mL) using a pressure-equalized addition funnel. The resulting mixture was stirred under reflux for 4 h and cooled down to room temperature. The precipitates were filtered off and the ether solution was washed with 1.0 N HCl (300 mL) and water (2×300 mL). The solvent was removed using a rotatory evaporator and the excess amount of diiodomethane was removed at ~70° C. under high vacuum to provide 140 g of the cyclopropanated trioleoylglycerol. The cyclopropanated trioleoylglycerol had an Iodine Value of 4.36 as compared to the Iodine Value of 83.5 for the starting trioleoylglycerol.

$^1$H-NMR (cyclopropanated trioleoylglycerol) (300 MHz, CDCl3) 5.26 (m, 1H), 4.31–4.10 (m, 4H), 2.30 (t, 6H, J=7.5 Hz), 1.28–1.25 (m, 78H), 0.86 (t, 9H, J=6.6 Hz), 0.63–0.51 (m, 10H), −0.33 to −0.37 (m, 2H); $^{13}$C-NMR (cyclopropanated trioleoylglycerol) (300 MHz, CDCl3) 173.2, 172.8, 68.8, 62.1, 34.2, 34.0, 31.9, 30.2, 30.1, 29.7, 29.5, 29.4, 29.3, 29.1, 29.0, 28.7, 28.6, 24.9, 24.8, 22.7, 15.8, 15.7, 14.1, 10.9. Raman Shift (cm-1) (cyclopropanated trioleoylglycerol, neat): 3066, 2994, 2932, 2896, 2855, 1747, 1442, 1396, 1298. IR (cm-1) (cyclopropanated trioleoylglycerol, neat): 3080, 3000, 2932, 1032.

$^1$H-NMR (trioleoylglycerol) (300 MHz, CDCl3) 5.34–5.30 (m, 7H), 4.31–4.10 (m, 4H), 2.30 (t, 6H, J=7.5 Hz), 2.00–1.96 (m, 12H), 1.28–1.25 (m, 66H), 0.86 (t, 9H, J=6,6 Hz). $^{13}$C-NMR (trioleoylglycerol) (300 MHz, CDCl3) 173.2, 172.8, 129.9, 129.6, 68.8, 62.1, 34.1, 34.0, 31.9, 29.8, 29.7, 29.5, 29.2, 29.1, 29.0, 27.2, 27.1, 24.9, 24.8, 22.7, 14.1. Raman Shift (cm-1) (trioleoylglycerol, neat): 3010, 2927, 2896, 2855, 1747, 1659, 1437, 1303, 1262. IR (cm-1) (trioleoylglycerol, neat): 3010.

Example 2—Cyclopropanation of a High Oleic Canola Oil

To a suspension of 100 g of freshly prepared zinc-copper couple (III) in dry diethyl ether (500 mL) stirred mechanically under reflux was added dropwise a solution of 130 g of CV-75 (a high oleic canola oil stock commercially available from Inter Mountain Canola, Idahofalls, Id.) and 433 g of diiodomethane in dry diethyl ether (100 mL) using a pressure-equalized addition funnel. The resulting mixture was stirred under reflux for 4 h and cooled down to room temperature. The precipitates were filtered off and the ether solution was washed with 1.0 N HCl (300 mL) and water (2×300 mL). The solvent was removed using a rotatory evaporator and the excess amount of diiodomethane was removed at ~70° C. under high vacuum to provide 140 g of cyclopropanated CV-75.

Raman Shift (cm-1) (cyclopropanated CV-75, neat): 3066, 2994, 2932, 2896, 2855, 1747, 1442, 1396, 1298, 1215. IR (cm-1) (cyclopropanated CV-75, neat): 3080, 3000, 2932, 1032.

Raman Shift (cm-1) (CV-75, neat): 3010, 2927, 2896, 2855, 1747, 1659, 1437, 1303, 1262. IR (cm-1) CV-75, neat): 3010.

Example 3—DSC of Cyclopropanated Adducts

Figure 1:
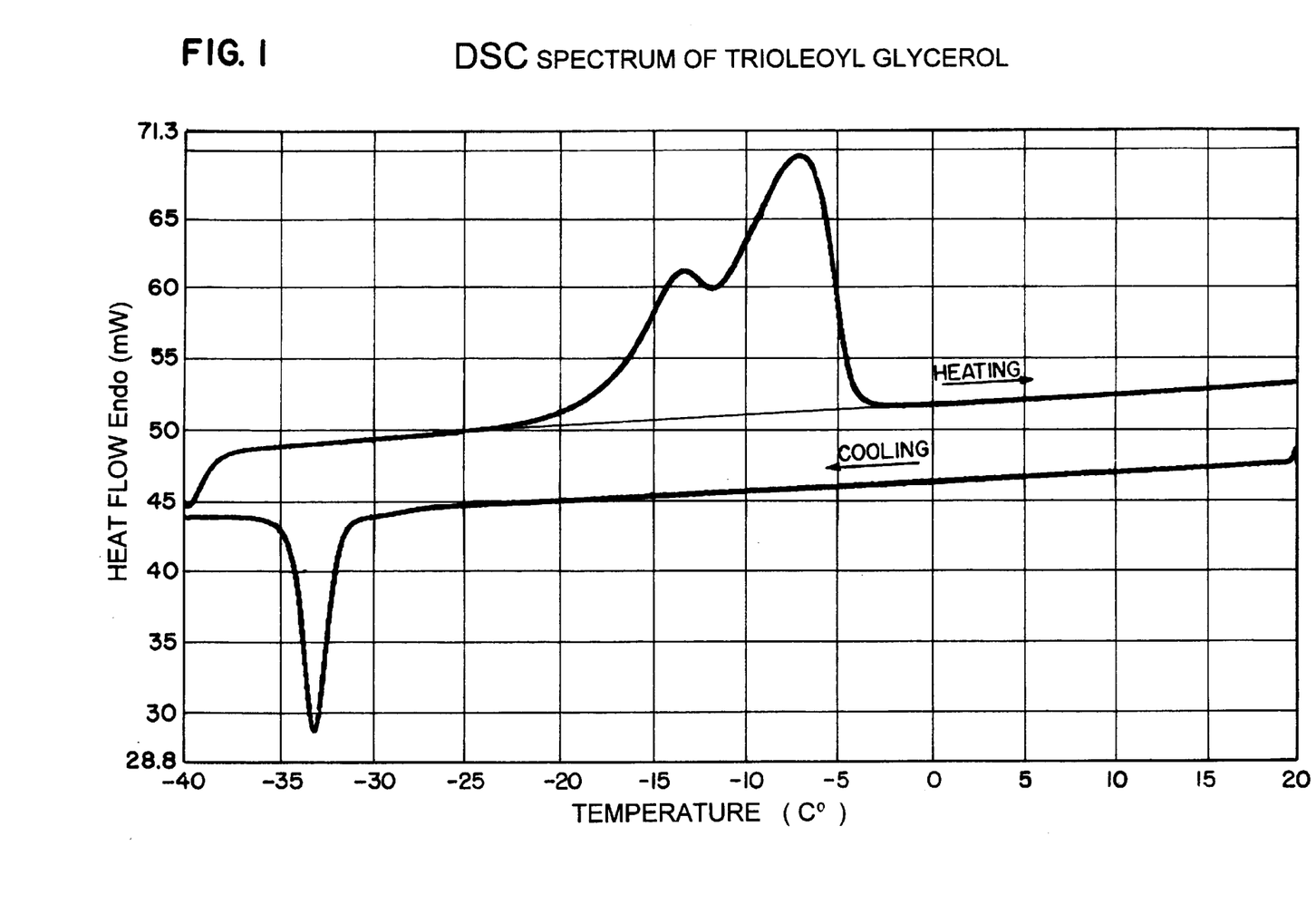
FIG. 1 shows a differential scanning calorimetry ("DSC") trace observed on cooling a sample of trioleoylglycerol from 0° C. to –40° C. at 1.00° C./min (lower curve) and then, after holding the sample at –40° C. for ten minutes, reheating the sample to 20° C. at a rate of 5.00° C./min (upper curve).
Figure 2:
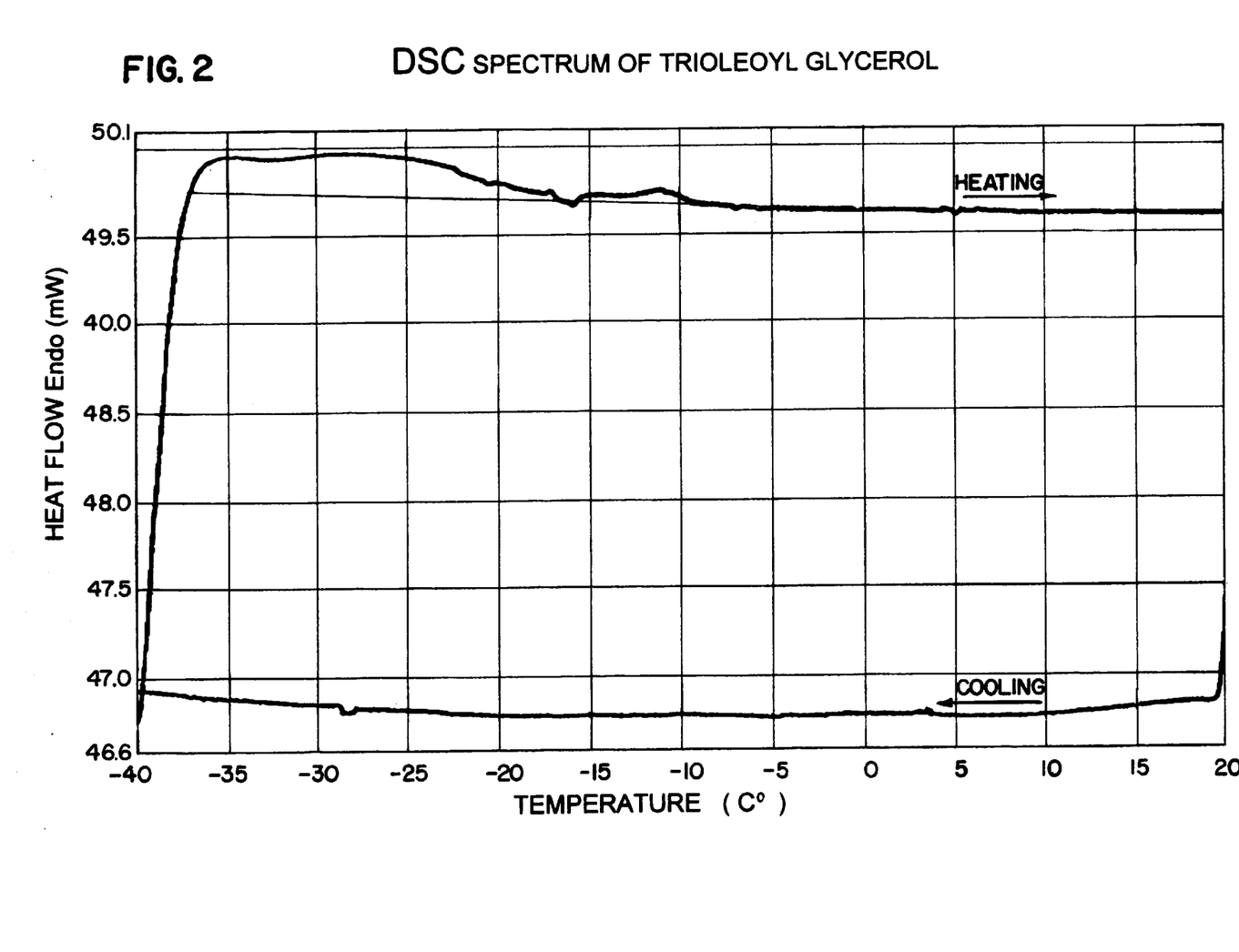
FIG. 2 shows a DSC trace observed on cooling a sample of cyclopropanated trioleoylglycerol from 0° C. to –40° C. at 1.00° C./min (lower curve) and then, after holding the sample at –40° C. for ten minutes, reheating the sample to 20° C. at a rate of 5.00° C./min (upper curve).

Differential scanning calorimetry ("DSC") samples of trioleoylglycerol, cyclopropanated trioleoylglycerol, CV-75, and cyclopropanated CV-75 were prepared and loaded at room temperature. The crystallization temperature ($T_c$), melting temperature ($T_m$) and deltaH were determined for these samples using the following sequence: a) hold the sample at 20° C. for 10.0 min; b) cool the sample to −40° C.

at a rate of 1.00° C./min; c) hold the sample at −−40° C. for 10.0 min; d) heat the sample to 20° C. at a rate of 5.00° C./min. The DSC results are summarized below. FIGS. 1 and 2 show the DSC curves obtained for trioleoylglycerol and cyclopropanated trioleoylglycerol respectively. The results demonstrate that cyclopropanation can substantially decrease the enthalpy of melting of a vegetable oil.

Cyclopropanated trioleoylglycerol: Tc=not observed; Tm=$^-$20–$^-$22° C.; deltaH=2 J/g.

Trioleoylglycerol: Tc=−33° C.; Tm=−5° C.; deltaH=72 J/g.

Cyclopropanated CV-75: Tc=not observed; Tm=−10° C.; deltaH=4 J/g. CV-75: Tc=−40° C.; Tm=-7° C.; deltaH= 67.5 J/g.

Example 4 —Oxidative Stability of Cyclopropanated Adducts

The oxidative stability of the cyclopropanated products produced in Examples 1 and 2 as well as the corresponding starting materials (trioleoylglycerol and CV-75) were determined by treating samples using the procedure described in A.O.C.S. Method Cd 12b-92. The Oxidized Viscosity Index ("OVI") was measured by passing a controlled flow of air through a heated sample of the oil. The degradation of the sample under such conditions typically includes an induction phase followed by a large increase in the rate of oxidation and/or polymerization with an associated large increase in the viscosity of the sample after this point. The viscosity after the induction phase was complete and the length of time (to the nearest hour) required for the oil sample to complete the induction period is reported below. The results shown below demonstrate that cyclopropanation can substantially decrease the enthalpy of melting of a vegetable oil.

Viscosity before and after Oxidative Stability Testing
Trioleoylglycerol:
    Untreated: 80 cP;
    After OSI: 1494 cP (3.65 hr).
Cyclopropanated trioleoylglycerol:
    Untreated: 190 cP;
    After OSI: 277 cP (16.05 hr).
CV-75 with 1% TBHQ:
    Untreated: 68 cP;
    After OSI: circa 1500 cP (150.4 hr).
Cyclopropanated CV-75 with 1% TBHQ:
    Untreated: 194 cP;
    After OSI: 300 cP (211.75 hr).

The viscosity results were corroborated by examining the Raman spectra of the various samples before and after being subjected to Oxidative Stability Index testing conditions ("OSI"). The results are shown in FIGS. 3–6.

Figure 3:
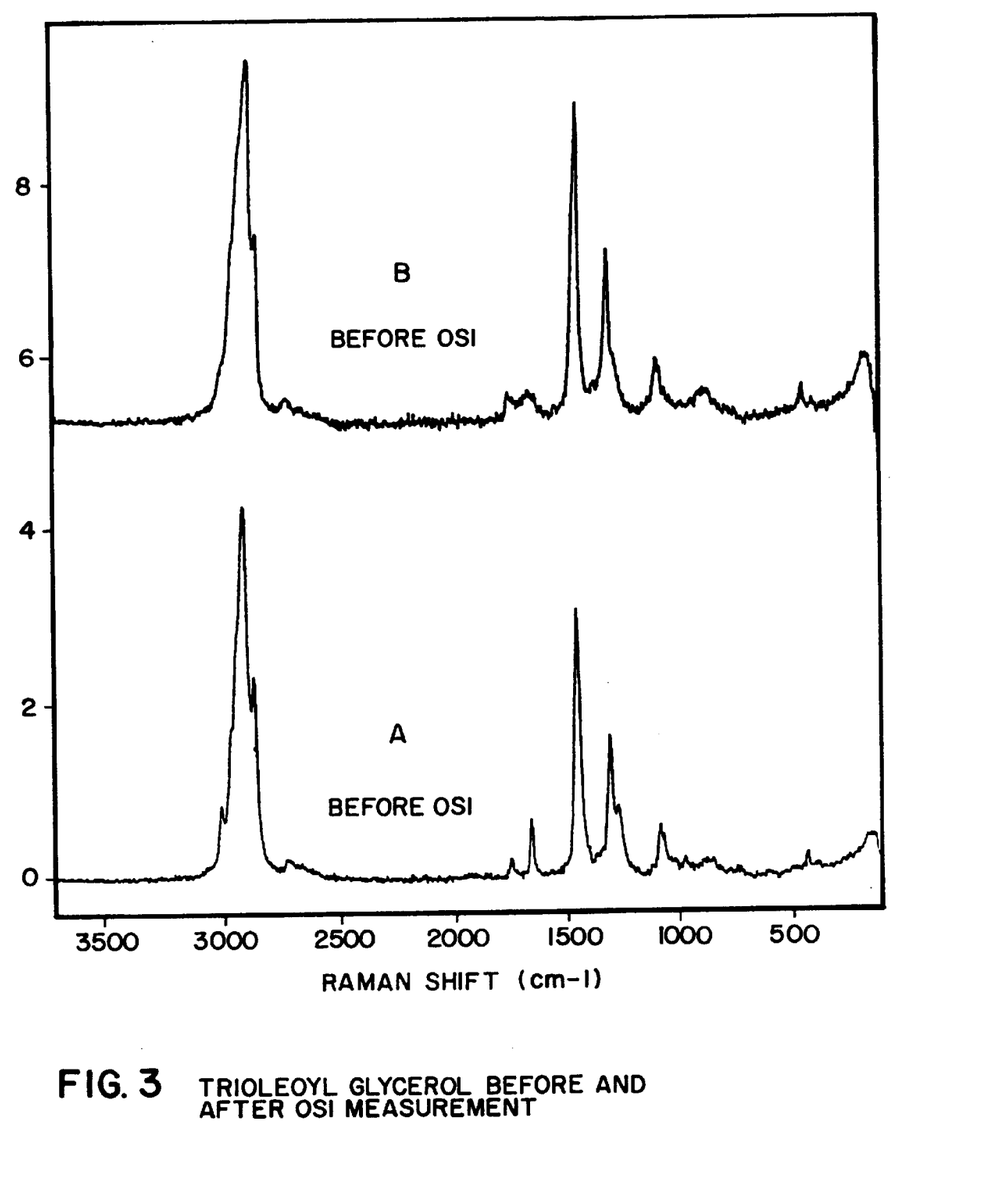
FIG. 3 shows Raman spectra of (A) untreated trioleoylglycerol; and (B) trioleoylglycerol after being treated by passing oxygen through a 110° C. sample for 3.65 hours.
Figure 4:
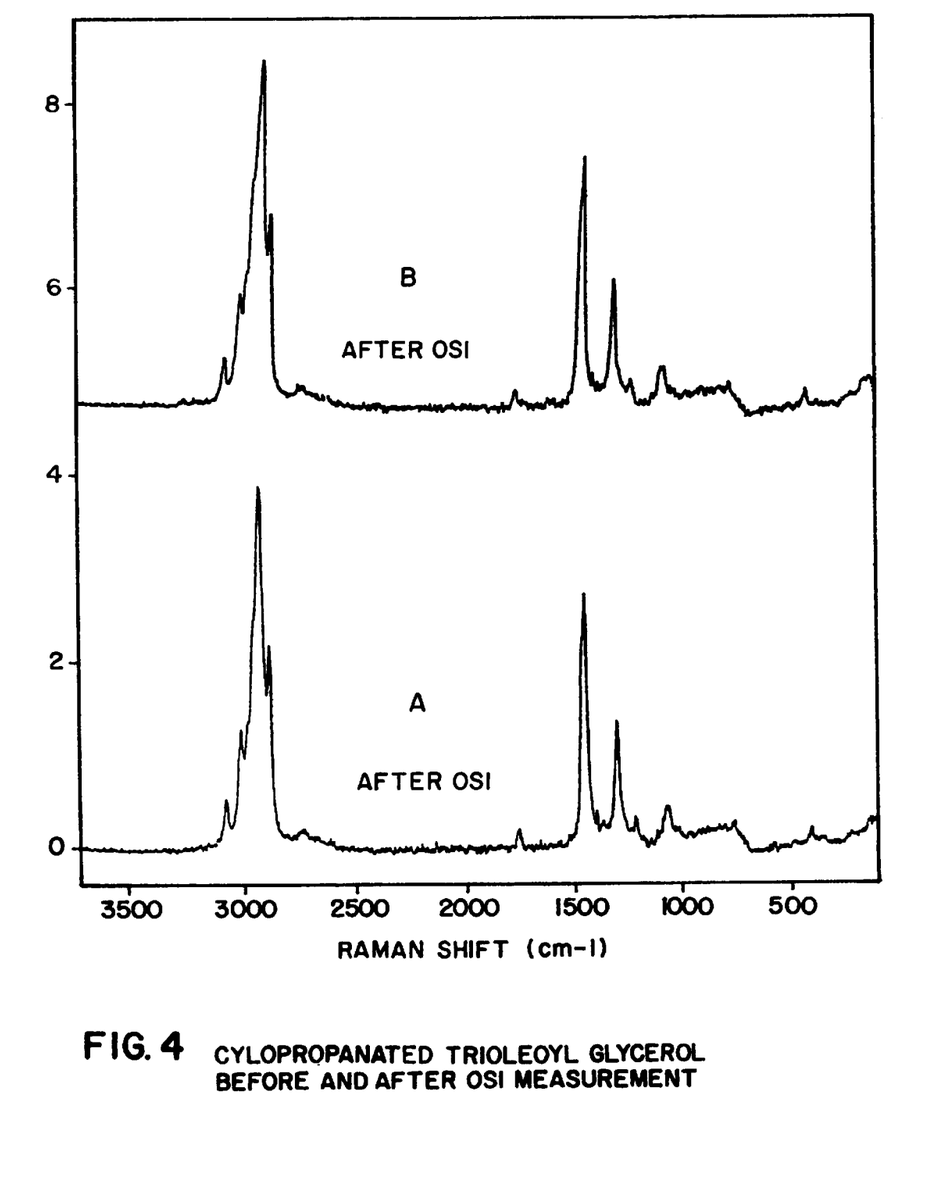
FIG. 4 shows Raman spectra of (A) untreated cyclopropanated trioleoylglycerol; and (B) cyclopropanated trioleoylglycerol after being treated by passing oxygen through a 110° C. sample for 16.05 hours.

FIG. 3 shows the Raman spectra of untreated trioleoylglycerol (A) and trioleoylglycerol after being subjected to OST (B). The spectra show a substantial changes in the peaks at 1262, 1659 and 1747. In contrast, as shown in FIG. 4, the Raman spectra of untreated cyclopropanated trioleoylglycerol (A) and cyclopropanated trioleoylglycerol after being subjected to OST (B) are essentially identical.

Figure 5:
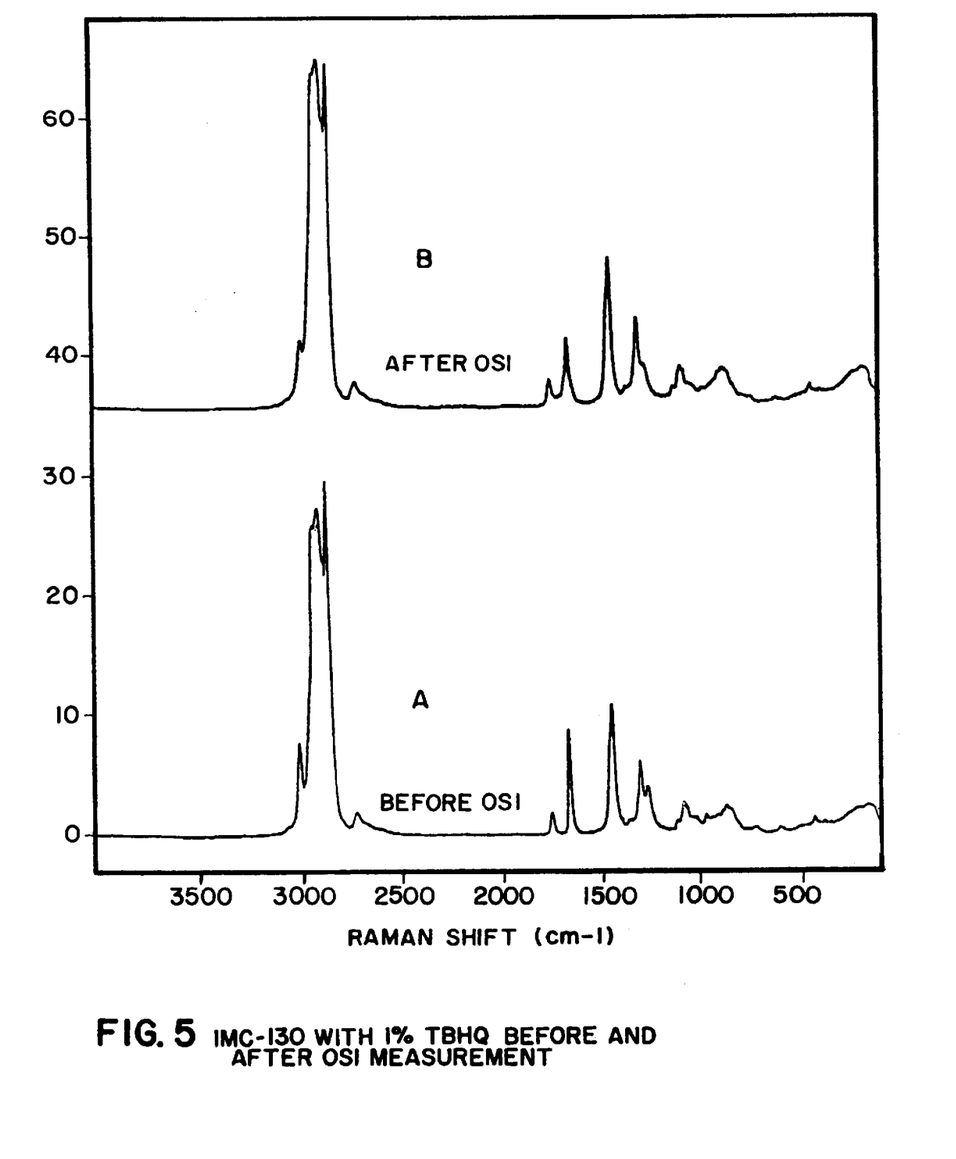
FIG. 5 shows Raman spectra of (A) untreated CV-75 with 1% t-butylhydroquinone ("TBHQ"); and (B) CV-75 with 1% TBHQ after being treated by passing oxygen through a 110° C. sample for 150.4 hours.
Figure 6:
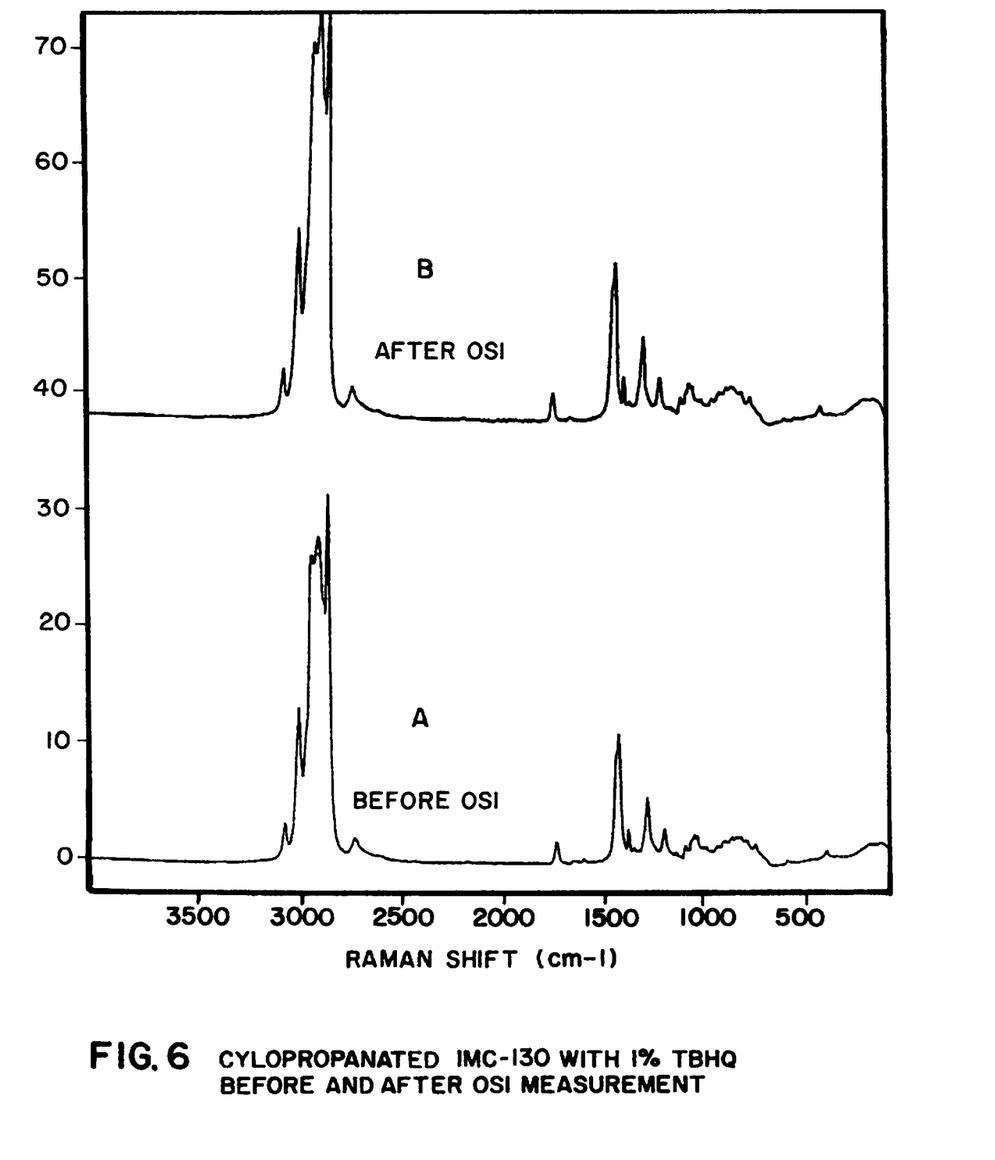
FIG. 6 shows Raman spectra of (A) untreated cyclopropanated CV-75 with 1% TBHQ; and (B) cyclopropanated CV-75 with 1% TBHQ after being treated by passing oxygen through a 110° C. sample for 211.75 hours.

FIG. 5 shows the Raman spectra of untreated CV-75 with 1% TBHQ (A) and CV-75 with 1% TBHQ after being subjected to OST (B). The spectra show a substantial changes in the peaks at 1262, 1659 and 1747. In contrast, as shown in FIG. 6, the Raman spectra of untreated cyclopropanated CV-75 with 1% TBHQ (A) and cyclopropanated CV-75 with 1% TBHQ after being subjected to OST (B) are essentially identical.

What is claimed is:

1. A process for modifying an unsaturated polyol fatty acid ester stock comprising:
    reacting the unsaturated polyol fatty acid ester stock with a non-enzymatic cyclopropanating agent to form a cyclopropanated product comprising fatty acid ester which has at least one polyol fatty acyl chain modified to include a cyclopropyl group, wherein the cyclopropanated product has a pour point of no more than 0° C.

2. The process of claim 1 wherein the cyclopropanated product has an $OV_{50}$ value which is at least about 50% higher than that of the unsaturated polyol fatty acid ester stock.

3. The process of claim 1 wherein the unsaturated polyol fatty acid ester stock includes unsaturated triacylglycerol oil.

4. The process of claim 1 wherein the unsaturated polyol fatty acid ester stock has an Iodine Value of no more than about 150.

5. The process of claim 1 wherein the unsaturated polyol fatty acid ester stock has an active methylene content of no more than about 0.8.

6. The process of claim 1 comprising reacting the unsaturated polyol fatty acid ester stock with a sufficient amount of cyclopropanating agent to form a cyclopropanated product having an average cyclopropyl content of at least about 0.25 cyclopropyl groups per fatty acyl chain.

7. The process of claim 1 comprising reacting the unsaturated polyol fatty acid ester stock with cyclopropanating agent which includes R'CHXY, wherein X is bromo, or iodo, Y is chloro, bromo or iodo, and R' is hydrogen or n-C(1–6) alkyl.

8. The process of claim 7 wherein the cyclopropanating agent further comprises zinc reagent.

9. The process of claim 8 wherein the zinc reagent is Zn(Cu), Zn(Ag) or $R_2Zn$, wherein R is n-C(1–6)alkyl.

10. The process of claim 8 wherein R'CHXY is $CH_2Br_2$ or $CH_2I_2$.

11. The process of claim 1 comprising reacting the unsaturated polyol fatty acid ester stock with cyclopropanating agent which is capable of adding :$CR^2R^3$ to a carbon—carbon double bond to form a cyclopropyl group, wherein $R^2$ is H, halo, n-alkyl, phenyl or substituted phenyl, and $R^3$ is H or halo.

12. The process of claim 8 wherein cyclopropanating agent which is capable of adding :$CH_2$, :$CCl_2$, or :$CBr_2$ to the carbon—carbon double bond to form the cyclopropyl group.

13. The process of claim 1 wherein the cyclopropanated product has an active methylene content at least about 10% lower than that of the unsaturated polyol fatty acid ester stock.

14. The process of claim 1 comprising reacting the unsaturated polyol fatty acid ester stock with sufficient cyclopropanating agent to form a cyclopropanated product having an OVI of at least about 50 hours.

15. The process of claim 1 wherein the cyclopropanated product has an enthalpy of melting which is at least about 10 J/g lower than that of the unsaturated polyol fatty acid ester stock.

16. The process of claim 1 wherein said fatty acid ester of a polyol is selected from the group consisting of glycerol, ethylene glycol, diethylene glycol, triethylene glycol, neopentylglycol, pentaerythritol, trimethylolethane, trimethylolpropane, sorbitol, cyclohexanediol, inositol, glucose, galactose, sorbose and mixtures thereof.

17. The method of claim 1 wherein said fatty acid ester of a polyol is selected from the group consisting of glycerol, pentaerythritol, trimethylolethane, trimethylolpropane, sorbitol, inositol, glucose, galactose, sorbose and mixtures thereof.

18. The process of claim 1, wherein the cyclopropanated product has an active methylene content of no more than 0.5.

19. The process of claim 1, wherein the cyclopropanated product and an active methylene content of no more than 0.1.

20. A modified unsaturated triacylglycerol oil comprising triacylglycerols which include at least one unsaturated fatty acyl chain modified to include a cyclopropyl group; wherein said modified unsaturated triacylglycerol oil has a pour point of no more than about 0° C. and an active methylene content of no more than about 0.1.

21. The modified unsaturated triacylglycerol oil of claim 20 having an average cyclopropyl content of at least about 0.25 cyclopropyl groups per fatty acyl chain.

22. The modified unsaturated triacylglycerol oil of claim 20 having an OVI of at least about 50 hours.

23. The modified unsaturated triacylglycerol oil of claim 20 having an Iodine Value of no more than about 130.

24. A method for producing a lubricant comprising:
   reacting an unsaturated polyol fatty acid ester stock with a non-enzymatic cyclopropanating agent to form a cyclopropanated product including at least one fatty acyl having at least one cyclopropyl group of an unsaturated polyol fatty acid ester wherein the cyclopropanated product has a pour point of no more than 0° C.

25. The method of claim 24 further comprising blending the cyclopropanated product with a petroleum based lubricant base stock.

26. The method of claim 24, wherein the cyclopropanated product has an active methylene content of no more than 0.5.

27. The method of claim 24, wherein the cyclopropanated product has an active methylene content of no more than 0.1.

28. A lubricant comprising polyol fatty acid ester which includes at least one fatty acyl chain having a cyclopropyl group; wherein the polyol fatty acid ester has a pour point of no more than about 0° C. and an active methylene content of no more than about 0.1.

29. The lubricant of claim 28 wherein said lubricant is a crankcase oil, transmission oil, power transfer fluid, gear oil, metal-working lubricant or grease.

30. A process for producing a lubricant base stock comprising:
   reacting an unsaturated polyol fatty acid ester stock having an Iodine Value of no more than about 150 with a non-enzymatic cyclopropanating agent to form a cyclopropanated product comprising fatty acid ester which includes at least one unsaturated polyol fatty acyl chain modified to include a cyclopropanated adduct wherein the cyclopropanated product has a pour point of no more than 0° C.

31. The process of claim 30, wherein the cyclopropanated product has an active methylene content of no more than 0.5.

32. The process of claim 30, wherein the cyclopropanated product has an active methylene content of no more than 0.1.

33. A lubricant formed by a process comprising:
   reacting a non-enzymatic cyclopropanating agent with an unsaturated polyol fatty acid ester stock to form a cyclopropanated product which includes fatty acid ester having at least one unsaturated fatty acyl chain modified to include a cyclopropanated adduct wherein the cyclopropanated product has an OVI of at least about 50 hours.

34. A method of reducing friction between moving parts comprising applying a lubricant to at least one of said moving parts, wherein the lubricant comprises a cyclopropanated product which includes at least one unsaturated polyol fatty acid ester modified to comprise at least one fatty acyl chain including a cyclopropyl group; wherein the cyclopropanated product has an OVI of at least about 50 hours.

35. A method of disposing of a used lubricant comprising biodegrading the used lubricant;
   wherein the used lubricant is derived from a lubricant comprising a cyclopropanated product which includes at least one unsaturated polyol fatty acid ester modified to have at least one fatty acyl chain including a cyclopropyl group; wherein the cyclopropanated product has an OVI of at least about 50 hours.

36. A process for modifying an unsaturated polyol fatty acid ester stock comprising:
   reacting the unsaturated polyol fatty acid ester stock with a non-enzymatic cyclopropanating agent to form a cyclopropanated product comprising fatty acid ester which has at least one unsaturated polyol fatty acyl chain modified to include a cyclopropyl group, wherein the cyclopropanated product has a pour point which is lower than that of the unsaturated polyol fatty acid ester stock.

37. An polyol fatty acid ester comprising at least one fatty acyl chain which includes a cyclopropyl group; wherein the polyol fatty acid ester has a pour point of no more than about 0° C. and an active methylene content of no more than about 0.1.

38. The polyol fatty acid ester of claim 37 having an OVI of at least about 50 hours.

39. A lubricant comprising:
   a lubricant base stock which includes at least about 50 wt % of a modified unsaturated triacylglycerol oil prepared by reacting an unsaturated polyol fatty acid ester stock with cyclopropanating agent to form a cyclopropanated product including at least one fatty acyl having at least one cyclopropyl group of an unsaturated polyol fatty acid ester.

* * * * *